(12) United States Patent
Bernan et al.

(10) Patent No.: US 7,019,014 B2
(45) Date of Patent: Mar. 28, 2006

(54) PROCESS FOR PRODUCING ANTICANCER AGENT LL-D45042

(75) Inventors: Valerie S. Bernan, New City, NY (US); Edmund I. Graziani, Ridgewood, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/842,277

(22) Filed: May 10, 2004

(65) Prior Publication Data

US 2004/0229323 A1 Nov. 18, 2004

Related U.S. Application Data

(60) Provisional application No. 60/469,719, filed on May 12, 2003.

(51) Int. Cl.
| | |
|---|---|
| A01N 43/42 | (2006.01) |
| A01N 63/00 | (2006.01) |
| A61K 31/44 | (2006.01) |
| C12P 1/00 | (2006.01) |
| C12P 33/00 | (2006.01) |

(52) U.S. Cl. .................. 514/291; 435/41; 435/53; 424/93.43

(58) Field of Classification Search ............ 435/410, 435/41, 53; 424/122, 93.43
See application file for complete search history.

(56) References Cited

U.S. PATENT DOCUMENTS 5,093,338 A  3/1992  Byrne et al.

FOREIGN PATENT DOCUMENTS

| WO | WO 93/11130 | 6/1993 |
| WO | WO 93/16189 | 8/1993 |
| WO | WO 94/10843 | 5/1994 |
| WO | WO 94/18208 | 8/1994 |
| WO | WO 95/14023 | 5/1995 |

OTHER PUBLICATIONS

Randall Ellis Morris; Transplantation Reviews; vol. 6; pp. 39-87; 1992.
Tom S. Chen, et al.; The Journal of Antibiotics, vol. 45; pp. 118-123; 1992.
Hiroyuki Nishida, et al.; The Journal of Antibiotics; vol. 48; pp. 657-666; 1995.
Lake EE Khaw, et al.; Journal of Bacteriology; vol. 180; pp. 809-814; 1998.

*Primary Examiner*—Sandra E. Saucier
*Assistant Examiner*—Lora E Barnhart
(74) *Attorney, Agent, or Firm*—Daniel B. Moran

(57) ABSTRACT

The disclosure describes the production of anticancer agent LL-D45042, having the structure:

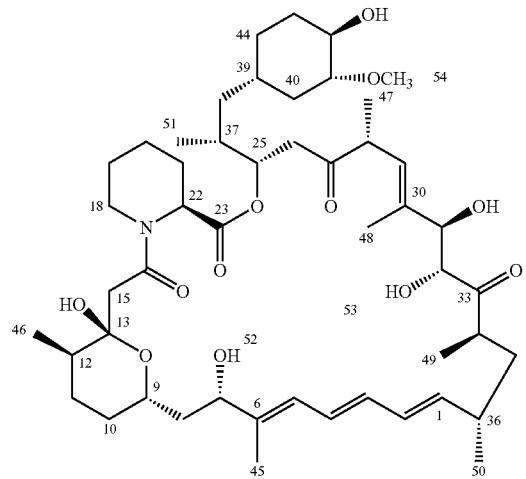

by fermentation, to methods for the recovery and concentration of this anticancer agent from crude solutions, and to processes for the purification of this anticancer agent as well as a new microorganism of the species *Streptomyces hygroscopicus* LL-D45042 and mutants thereof useful in the preparation of this compound.

3 Claims, 5 Drawing Sheets

PROCESS FOR PRODUCING ANTICANCER AGENT LL-D45042

"This application claims priority from copending provisional Application No. 60/469,719 filed May 12, 2003 the entire disclosure of which is hereby incorporated by reference".

FIELD OF THE INVENTION

The present invention relates to a process for producing an anticancer agent designated LL-D45042 by fermentation, to methods for its recovery and concentration from crude solutions and to a process for its purification. The present invention includes within its scope a novel strain of *streptomyces hygroscopicus* designated LL-D45042.

BACKGROUND OF THE INVENTION

Rapamycin a macrocyclic lactone has been shown to have antitumor activity (U.S. Pat. No. 4,885,171).

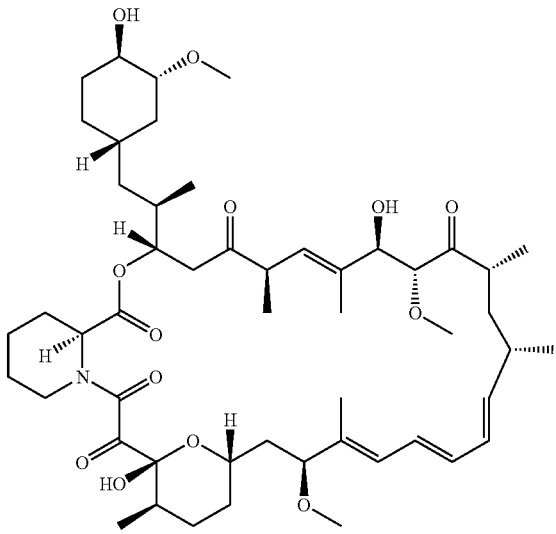

The biological effects of rapamycin are reviewed in Transplantation Reviews, 1992, 6, 39–87. Semisynthetic analogs of Rapamycin are described in WO 95/14023 and

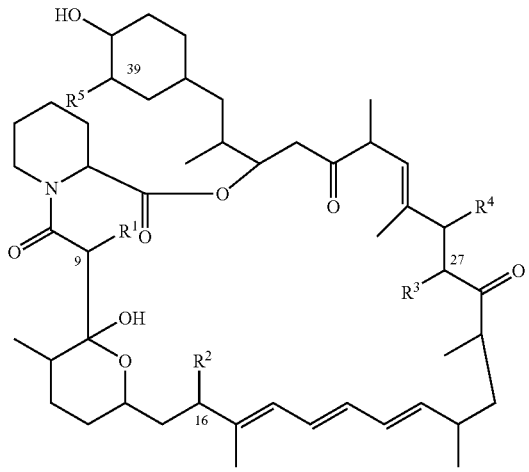

further described in WO 93/16189 are macrocyclic lactones produced by the cultures *Streptomyces hygroscopicus* (FERM BP-3688), *Actinoplanes* sp. (FERM BP-3832) or *Streptomyces toyocaensis* subsp.*humicola* (ATCC 39471) to produce macrocyclic lactones of the formula Additional Rapamycin analogs produced by fermentation means described in the art include: 7,29-bisdesmethyl-rapamycin (U.S. Pat. No. 5,093,338); 16-nor-rapamycin (WO 94/10843); 14-methylene rapamycin and 9-methylene rapamycin (WO 93/11130); 7,42-bis (O-demethyl)rapamycin (WO 94/18208) and a process to produce 7-O-dimethylrapamycin by cultivating ATCC 55368.

Microbial desmethylation of FK506/FR900520 by *actinoplanes* sp. ATCC 53771 forming products with immunosuppressive activity is reported by Tom S. Chen, et al., The Journal of Antibiotics, 45, 118–123 (1992).

Rapamycin structures formed by microbial manipulations of *Actinoplanes* sp. N902-109 are described by Hiroyuki Nishida, et al., The Journal of Antibiotics, 48, 657–666 (1995).

The precursor feedings and fermentation of *s. hygroscopicus* LEK III and the ability to synthesize rapamycins is reported by Lake II Khaw, et al., Journal of Bacteriology, 180, 809–14 (1998).

New antitumor compounds are continually in demand, for the treatment of cancer in man and the production of new macrolide anticancer compounds by fermentation means is an important feature of developing antitumor agents for further studies. Equally important are novel strains of cultures used in the production processes for preparing these compounds.

BRIEF SUMMARY OF THE INVENTION

The invention relates to the production of anticancer agent LL-D45042, by cultivation, to methods for the recovery and concentration of this anticancer agent from crude solutions, and to processes for the purification of this anticancer agent as well as a new microorganism useful in the preparation of this compound.

The invention includes within its scope the anticancer agent in diluted form, as crude concentrate and in pure form.

The anticancer agent designated LL-D45042 is formed during the cultivation under controlled conditions of a new strain of *Streptomyces hygroscopicus*, designated LL-D45042.

Cultivation means aerobic growth of an organism in the presence of assimilable sources of carbon, nitrogen and inorganic anion and cation salts.

The structure of LL-D45042 is:

The physicochemical characteristics of LL-D45042 are as follows:
a) Apparent molecular Formula: $C_{49}H_{77}NO_{12}$
b) Molecular Weight: Positive Ion Electrospray MS m/z=893.6 (M+Na)$^+$; Negative Ion Electrospray MS m/z=871.1 (M−H)$^−$; High Resolution Fourier Transform MS m/z=894.534230 (M+Na)$^+$
c) Proton Magnetic Resonance Spectrum: (500 MHz $d_6$-DMSO): See FIG. 1
d) Carbon-13 Magnetic Resonance Spectrum: (125 MHz $d_6$-DMSO): See FIG. 2
e) Infrared Absorbance Spectrum (thin film, NaCl plates): See. FIG. 3
f) Ultraviolet Absorption Spectrum: $\gamma_{max}$ nm (acetonitrile/water)=270, 280, 292: See FIG. 4

The anticancer agent LL-D45042 is formed during the cultivation under controlled conditions of *Streptomyces* strain designated LL-D45042.

This microorganism is maintained in the culture collection of Wyeth Research, Pearl River, N.Y. 10965, as culture LL-D45042. A viable culture of this microorganism is deposited under the Budapest Treaty with the Patent Culture Collection Laboratory, Northern Regional Research Center, U.S. Department of Agriculture, Peoria, Ill. 61604, and added to its permanent collection. Culture LL-D45042 has been assigned the NRRL accession number NRRL30642.

DESCRIPTION OF LL-D45042

Figure 1:
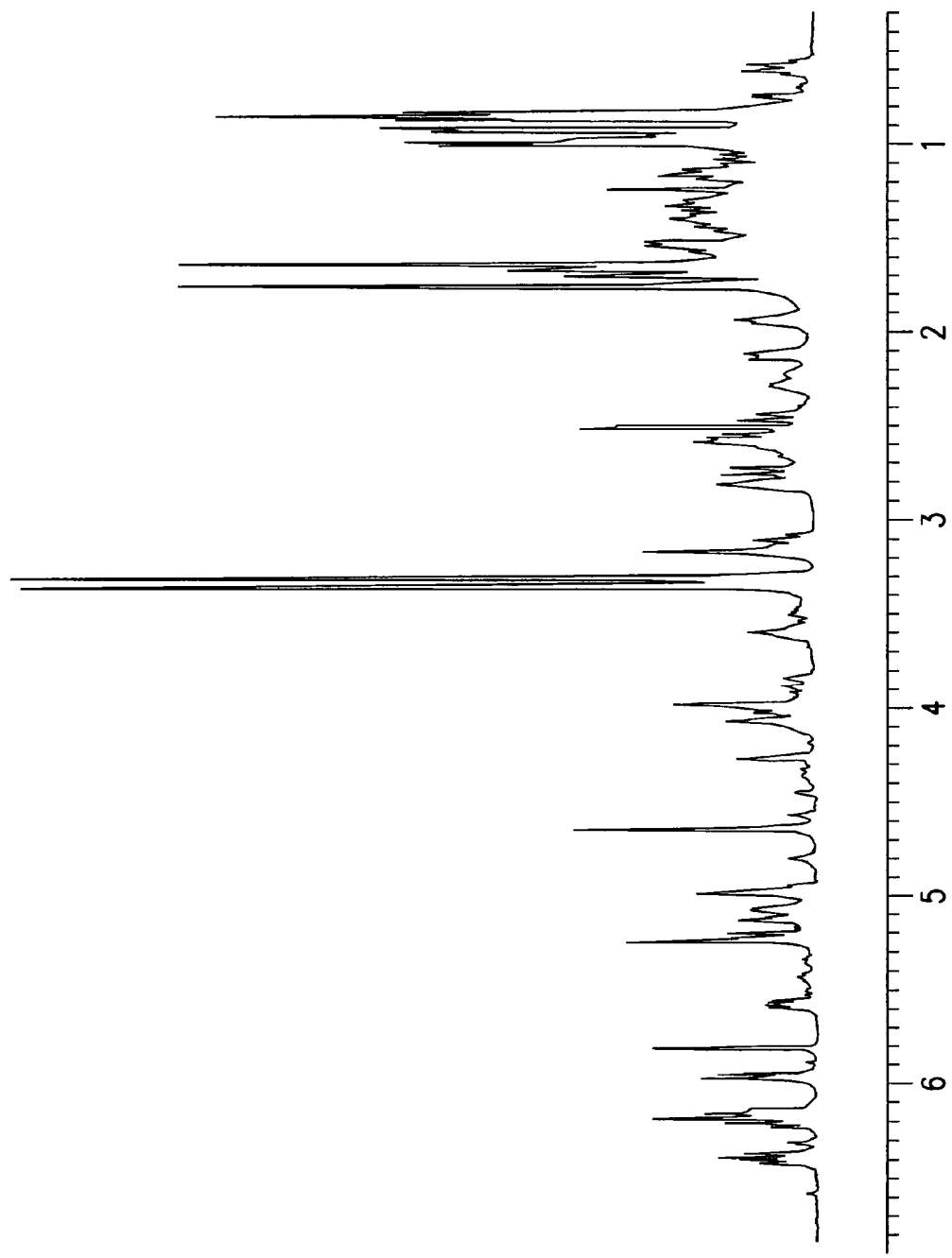
FIG. 1 Characteristic proton nuclear magnetic resonance (NMR) spectrum of LL-D45042 (500 MHz, $d_6$-DMSO).
Figure 2:
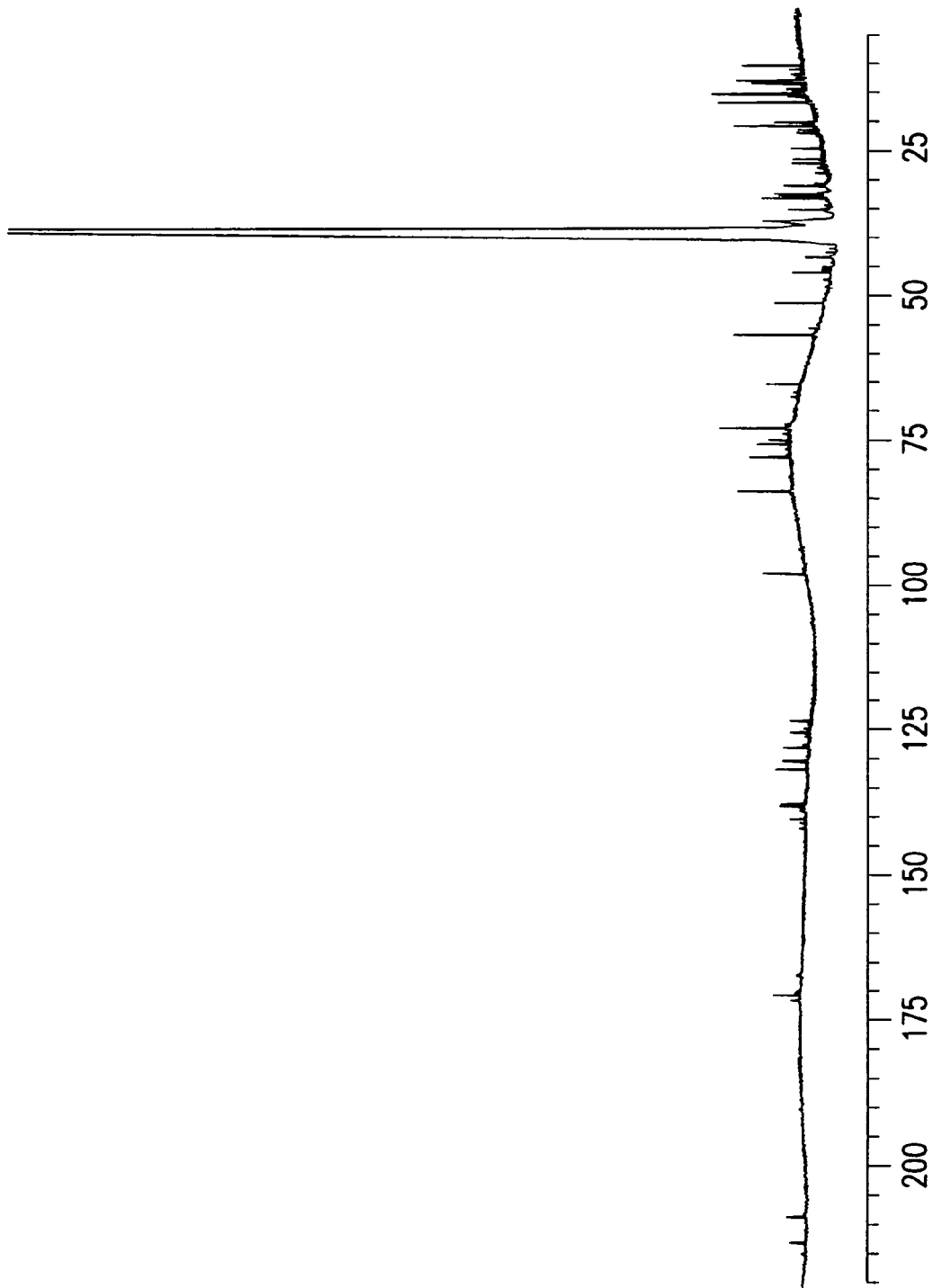
FIG. 2 Characteristic carbon nuclear magnetic resonance (NMR) spectrum of LL-D45042 (125 MHz, $d_6$-DMSO).
Figure 3:
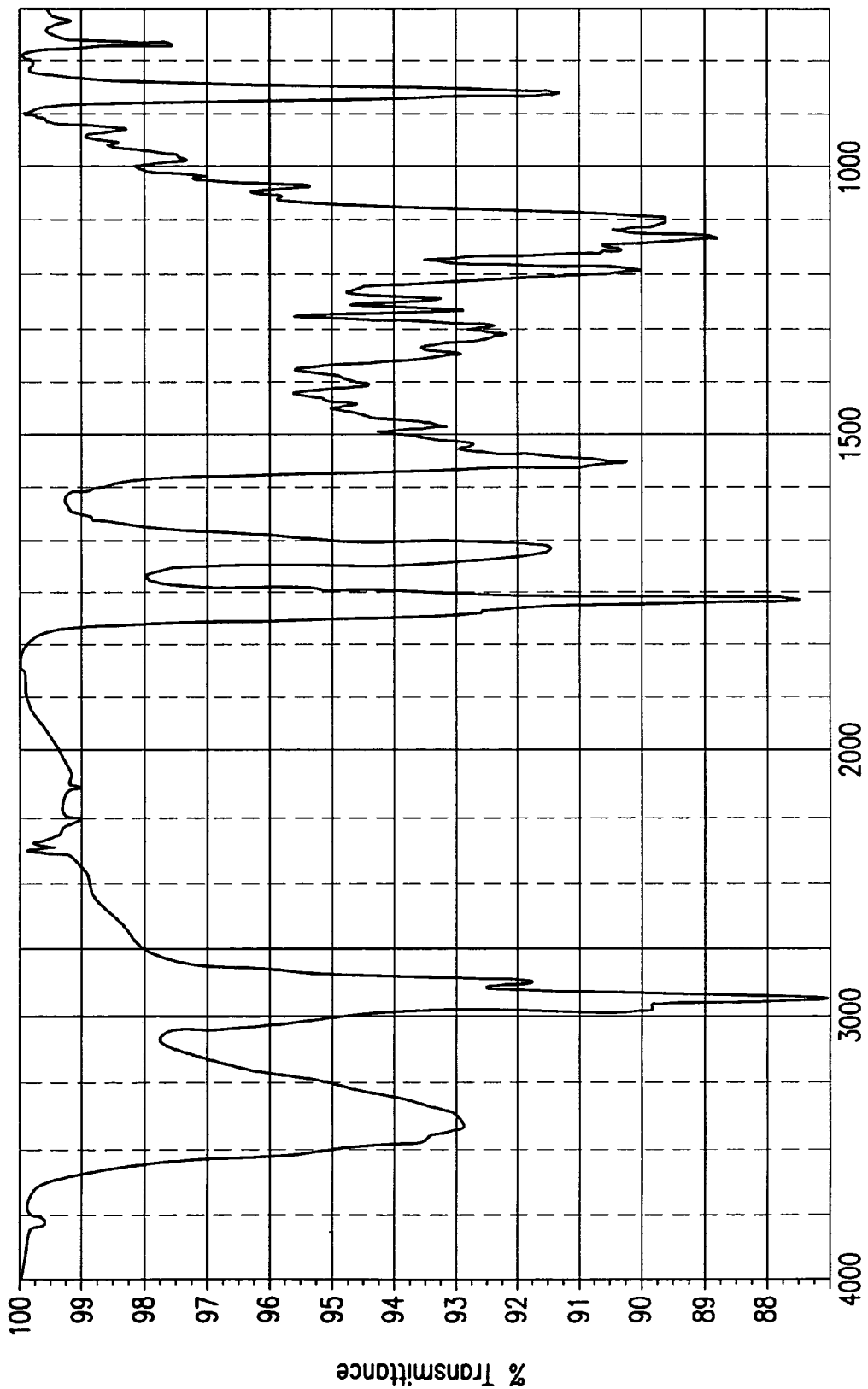
FIG. 3 Characteristic infrared (IR) spectrum of LL-D45042 (thin film, NaCl plates).
Figure 4:
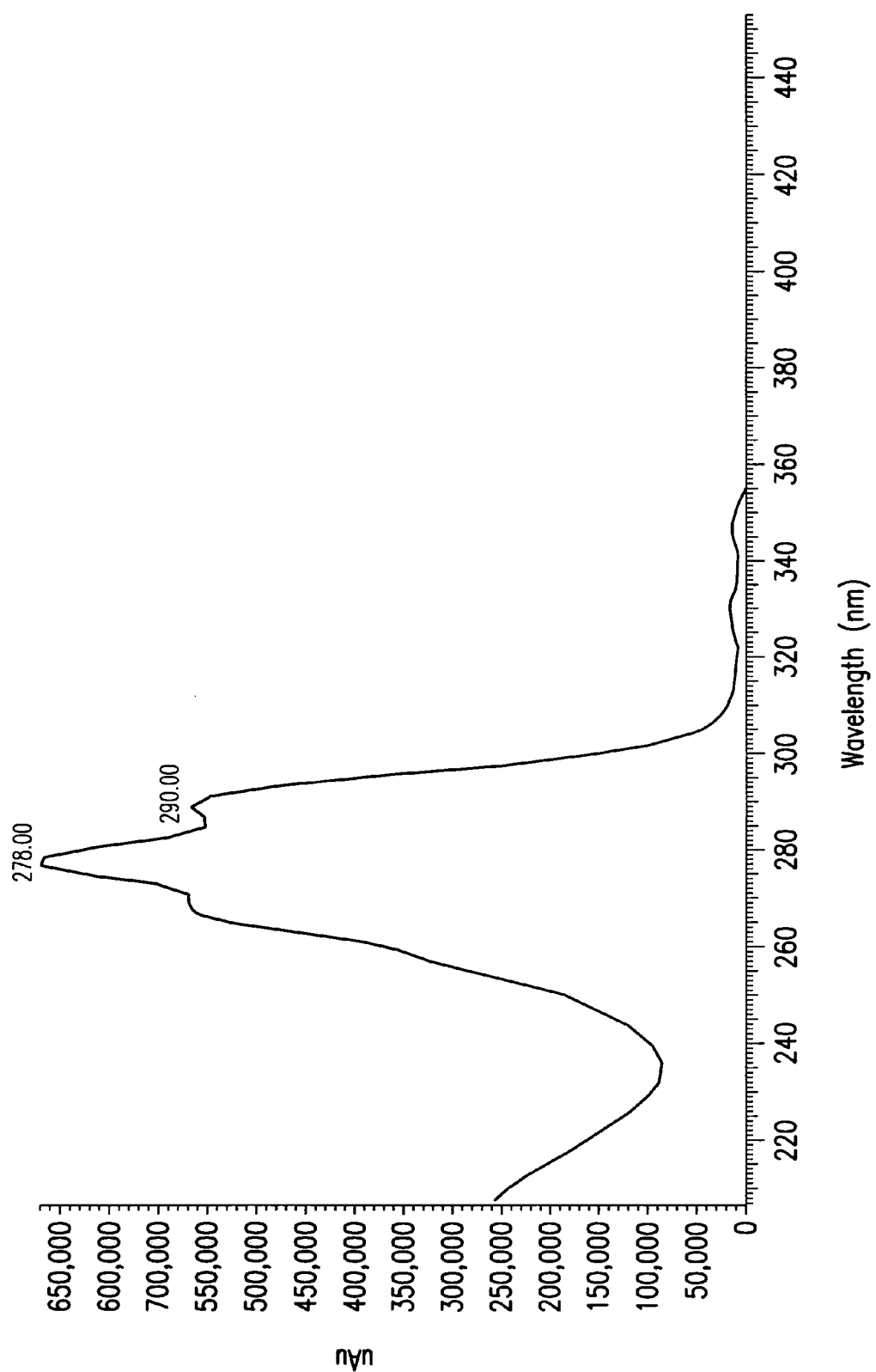
FIG. 4 Characteristic ultraviolet (UV) spectrum of LL-D45042 (acetonitrile/water).

The 16S rDNA sequence is determined for strain LL-D45042 following isolation and direct sequencing of the amplified gene. The nucleotide sequence is aligned with the sequences of previously studied streptomycetes, and phylogenetic trees are generated by using two neighbour-joining tree algorithms. The 16S rDNA sequence supported classification of the strain in the genus and species of *S. hygroscopicus*.

Observations are made of the cultural, physiological and morphological features of culture LL-D45042 using methods well known in the art. The macromorphology for culture LL-D45042 is described in Table 1

TABLE 1

Cultural characteristics of streptomycete strain LL-D45042

| Agar Medium | LL-D45042 | |
|---|---|---|
| Yeast-malt (ISP2) | G: | Rapid and abundant |
| | AM: | Dark grey yellow (91) |
| | SM: | Dark yellow (88) |
| | SP: | None |
| Oatmeal (ISP3) | G: | Very Abundant |
| | AM: | light grey (264) |

TABLE 1-continued

Cultural characteristics of streptomycete strain LL-D45042

| Agar Medium | LL-D45042 | |
|---|---|---|
| | SM: | light yellow brown (76) |
| | SP: | None |
| Inorganic salts-starch (ISP4) | G: | Very Abundant |
| | AM: | light grey (264) |
| | SM: | light olive brown to slight, yellow, brown (74, 94) |
| | SP: | None |
| Glycerol-Asparagine agar (ISP5) | G: | Abundant |
| | AM: | light grey (264) |
| | SM: | dark, grey, yellow (91) |
| | SP: | None |

G, growth; AM, aerial mycelium; SM, substrate mycelium; SP, soluble pigment ISCC, National Bureau of Standard Centroid Color Charts, Publication 440, Washington, D.C. 1976.

Culture LL-D45042 sporulates moderately to abundantly on most media studied. Aerial mycelium is monopodially branched; sporophores are terminated by spore chains in the form of short, narrow, compact and closed coils (Spiral) of three or more turns with ten or more spores present in each spiral. Spore color mass is predominately in the Grey-color series. Large spore masses predominate forming black hygroscopic patches after absorption of water, giving the appearance of black, gelatinous spots on the surface of several solid media.

Physiological studies from culture LL-D45042 resulted in no melanin production, slow starch hydrolysis, decomposition and fair growth on cellulose, no hydrogen sulfide production, and good digestion of casein. Carbohydrate utilization tests indicated good growth on: D-glucose, L-arabinose, sucrose, I-inositol, D-mannitol, β-D-fructose, α-L rhammnose, moderate growth on: D-xylose, and cellulose. Culture LL-D45042 exhibited abundant growth at 22° C., 28° C., and 37° C., but no growth at 45° C. and 50° C.

On the basis of the above properties, culture LL-D45042 is most similar to the properties of *Streptomyces hygroscopicus*. AYB-994 and *S. hygroscopicus* FERM BP-3688. A comparison of culture LL-D45042 to these two strains of *S. hygroscopicus* revealed several different characteristics. The cultural characteristics of culture LL-D45042 on glycerol-asparagine agar (ISP5) are abundant growth and dark, grey, yellow surface mycelium in contrast to the poor to moderate growth and cream to pale grey substrate mycelium on the comparison cultures. In addition culture LL-D45042 did not produce any soluble pigment on any of the ISP agars tested compared to a yellow to cream pigment produced by *S. hygroscopicus* AY B-994 and *S. hygroscopicus* FERM BP-3688. ISP carbon utilization tests are also different among the cultures. *S. hygroscopicus* FERM BP-3688 cannot utilize rhammnose and *S. hygroscopicus* AY B-994 cannot utilize sucrose or cellulose. Other differences include *S. hygroscopicus* FERM BP-3688 produced hydrogen sulfide, the other two cultures do not and culture LL-D45042 can decompose cellulose while the other *S. hygroscopicus* strains do not. These differences support the creation of a new strain of *S. hygroscopicus* designated LL-D45042.

For the production of this anticancer agent LL-D45042 the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques know to those skilled in the art such as for example, conjugation, transduction and genetic engineering techniques.

It is a further embodiment of the invention to provide a method of treating cancer in mammals in need thereof with an effective amount of LL-D45042 and pharmaceutically acceptable salts thereof.

It is an additional embodiment of the invention to provide a pharmaceutical composition of LL-D45042 and pharmaceutically acceptable salts thereof in the presence of one or more pharmaceutically acceptable carriers.

Biological Activity

Standard Pharmacological Test Procedures

Methods for In Vitro Anticancer Test Procedure

The in vitro anticancer activity of LL-D45042 is determined by measuring the concentration of compound required to inhibit the growth of 50% of cells in two tumour cell lines. Among the two tumor lines, it was previously established that the brain cancer line U87MG is highly sensitive to growth inhibition by rapamycin. The elevated sensitivity is due to its genetic mutation in the PTEN tumor suppressor gene leading to constitutive activation of mTOR signaling pathway. In contrast, the breast cancer line MDA435 does not harbor the PTEN mutation and exhibits a rapamycin-resistant phenotype. LL-D45042 is also evaluated in a binding assay of FKBP12, a cellular receptor of rapamycin, to determine its binding affinity. The results are given in Table 2, with $IC_{50}$'s reported in units of ng/mL.

TABLE 2

Antiproliferative and FKBP12 binding Activity for LL-D45042

|  | Growth Inhibition in Cells (ng/mL) | | Protein Binding (ng/mL) |
| --- | --- | --- | --- |
|  | U87MG | MDA435 | FKBP |
| LL-D45042 | 35 | >1000 | 350 |

These determinations are made by multi-dose testing of LL-D45042 and direct comparisons to the reference samples.

Figure 5:
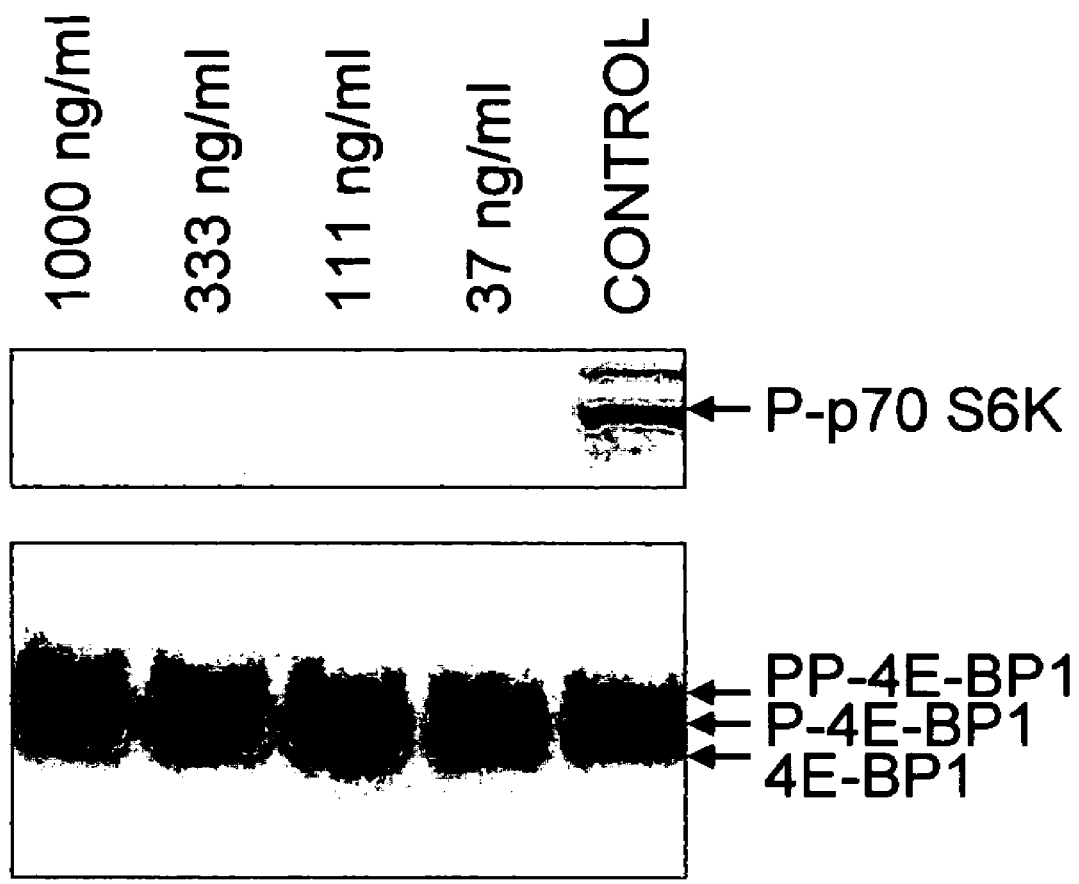
FIG. 5 Immunoblotting data for inhibition of cellular phosphorylation of p70 S6K1 and 4E-BP1 in LNCap prostate cancer cells by LL-D45042.

The inhibitors are further evaluated in the cellular phosphorylation assays by immunoblotting experiments for inhibition of mTOR substrate phosphorylation in LNCap prostate cancer cell model (see FIG. 5).

LL-D45042 derives its utility from its anticancer activity. In therapeutic use, the compound of this invention may be administered in the form of conventional pharmaceutical compositions appropriate for the intended use. Such compositions may be formulated as to be suitable for oral, parenteral or topical administration. The active ingredient may be combined in admixture with a nontoxic pharmaceutical carrier that may take a variety of forms depending on the form of preparation desired for administration, i.e. Oral, parenteral, or topical.

In therapeutic use, the compound of this invention may be administered in the form of conventional pharmaceutical composition appropriate for the intended use as an antibacterial. Such compositions may be formulated so as to be suitable for oral, parenteral or topical administration. The active ingredient may be combined in admixture with non-toxic pharmaceutical carrier may take a variety of forms, depending on the form of preparation desired for administration, i.e. oral, parenteral, or topical.

When the compound is employed as an anticancer agent, it may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from about 1 mg/kg of body weight to about 100 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the anticancer effective amount of LL-D45042 of the invention may be administered at a dosage and frequency without inducing side effects commonly experienced with conventional anticancer therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the anticancer effective amount of the LL-D45042 of the invention.

The active compound may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The active compound may also be administered parenterally or intraperitoneally. Solutions or suspensions of the active compound as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an anticancer effective amount of a compound of this invention and a pharmaceutically acceptable carrier.

The present invention further provides a method of treating cancer in warm-blooded animals including man, which comprises administering to the afflicted warm-blooded animals an anticancer effective amount of a compound or a pharmaceutical composition of a compound of the invention. The invention will be more fully described in conjunction with the following specific examples which are not to be construed as limiting the scope of the invention.

General Fermentation Conditions

Cultivation of actinomycete designated D45042 may be carried out in a wide variety of liquid culture media. Media which are useful for the production of hygroscopene include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium.

Further agitation in tanks is provided by a mechanical impeller. An antifoam agent such as silicon oil may be added as needed.

General Procedure for Preparation of LL-D45042

The cells from a 1 L culture of D45042 are pelleted by centrifugation and exhaustively extracted with 3×200 mL methanol over three days. The methanol extracts are combined, reduced in vacuo to yield an aqueous suspension that is subsequently taken to 200 mL total volume 80:20 water:methanol. This aqueous solution is extracted with three 150 mL portions of chloroform that are combined, dried over sodium sulfate, filtered, and reduced in vacuo to yield an orange gummy residue. This material is chromatographed on reversed phase silica (column: 250×20 mm YMC ODS-A RP) employing a gradient of from 30% methanol in water to 95% methanol in 60 minutes. The fraction containing crude LL-D45042 eluted with approximately 75% methanol ($t_R$=32 minutes). This fraction is further purified via reversed phase chromatography (column: 250×10 mm YMC ODS-A RP) employing a gradient from 5% acetonitrile in water to 95% acetonitrile in 20 minutes. Repeated fractionation of all the material obtained from methanolic extracts of mycelia from 1 L of D45042 yielded approximately 0.5 mg of a white solid, ($t_R$=28.9 min). HRFTESIMS: calcd for $C_{49}H_{77}NO_{12}Na$: 894.533799 found: 894.534230 (−0.00043); UV (acetonitrile-water): 270, 280, 292 nm; $^1H$ NMR ($CD_3CN$, 500 MHz) see FIG. 1.

We claim:

1. A pharmaceutical composition comprising an effective amount of a compound having the structure

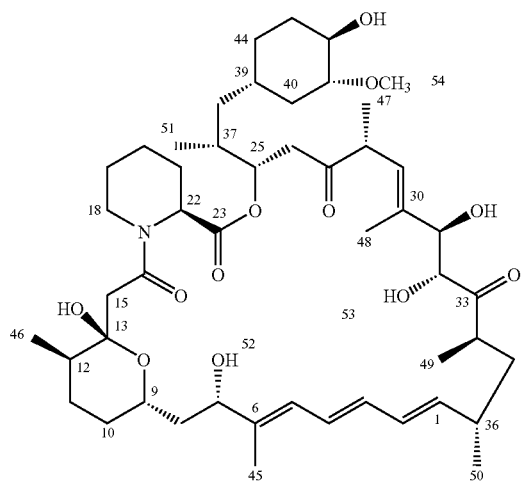

together with a pharmaceutical acceptable carrier.

2. An anticancer agent LL-D45042 produced by the process which comprises aerobically cultivating a biologically pure culture of *Streptomyces hygroscopicus* LL-D45042 or a LL-D45042 producing mutant thereof in a sterile liquid medium containing assimilable sources of carbon, nitrogen and inorganic anion and cation salts until LL-D45042 is formed and recovering and isolating LL-D45042.

3. A process for the preparation of LL-D45042 comprising cultivating a biologically pure culture of *Streptomyces hygroscopicus* LL-D45042 or a LL-D45042 producing mutant thereof under aerobic conditions, in a sterile liquid medium containing assimilable sources of carbon, nitrogen and inorganic anion and cation salts, until LL-D45042 is formed; and recovering and isolating LL-D45042.

* * * * *